United States Patent [19]

Wojcik

[11] 4,280,580

[45] Jul. 28, 1981

[54] PROXIMITY DETECTOR SYSTEM FOR A MEDICAL DIAGNOSTIC DEVICE

[75] Inventor: Dennis J. Wojcik, Waukesha, Wis.

[73] Assignee: General Electric Company, Milwaukee, Wis.

[21] Appl. No.: 957,531

[22] Filed: Nov. 3, 1978

[51] Int. Cl.³ .............................................. B60T 7/12
[52] U.S. Cl. ................................. 180/169; 246/187 C; 303/100; 307/360; 340/661
[58] Field of Search ....................... 180/167, 169, 275; 303/92, 95; 246/187 C; 343/7 VM, 7 VC; 367/96, 909; 307/360; 340/661

[56] References Cited

U.S. PATENT DOCUMENTS

| | | | |
|---|---|---|---|
| 3,152,326 | 10/1964 | Merlo | 343/7 VM |
| 3,192,382 | 6/1965 | Allison | 180/179 X |
| 3,493,920 | 2/1970 | MacMunn | 367/96 |
| 3,513,931 | 5/1970 | Warner et al. | 180/169 |
| 4,026,654 | 5/1977 | Beaurain | 180/169 X |
| 4,079,802 | 3/1978 | Kawata | 303/100 X |
| 4,084,149 | 4/1978 | Driver et al. | 367/96 X |

Primary Examiner—Randolph A. Reese
Assistant Examiner—D. W. Underwood
Attorney, Agent, or Firm—Douglas E. Stoner; Dana F. Bigelow

[57] ABSTRACT

A mobile medical diagnostic device having a mobility chassis with two supporting wheels and a central steerable drive wheel. The device has an electrical power steering system controlled by two synchronized handles operable by wrist action of an operator walking behind the device. The handles include a rotatable grip for controlling the velocity of the device. Advancing the grip actuates the throttle to the drive wheel and retarding the grip actuates a proportional electromechanical braking system. The device includes a proximity detector system which uses ultrasonic transducers to determine when an obstacle is within close proximity to the device, and automatically actuates the brake system. A window signal is established on the basis of both a preselected distance from the device within which it is desirable to apply the brakes, and a delay function which is determined by the distance of the front portion of the device from the transducer. If an object is within the window, the brakes are automatically actuated.

12 Claims, 7 Drawing Figures

PROXIMITY DETECTOR SYSTEM FOR A MEDICAL DIAGNOSTIC DEVICE

RELATED CASES

A steering and throttling system for a mobile device is claimed in copending U.S. application Ser. No. 957,532, filed Nov. 3, 1973 and assigned to the same assignee as the present invention. A braking system for a mobile device is claimed in copending U.S. application Ser. No. 957,533, filed Nov. 3, 1978 and assigned to the same assignee as the present invention. A stabilization system for a mobile device is claimed in U.S. application Ser. No. 957,530, filed Nov. 3, 1978 and assigned to the same assignee as the present invention.

BACKGROUND OF THE INVENTION

The present invention relates generally to a proximity detector system for a device having a self-propelled chassis. More particularly, the invention relates to an ultrasonic detector system for a medical diagnostic device which automatically stops the device when an obstacle is detected to be in close proximity to the front of the device.

Various types of equipment are made mobile by mounting the equipment on a self-propelled chassis. Mobility is particularly significant for medical diagnostic equipment, such as an X-ray device and a scintillation camera device for obtaining diagnostic images of a patient. In many cases, the patient requires intensive care or critical care and cannot be moved, so the diagnostic device must be transported to the patient. The device may be required to be operated virtually anywhere in the hospital. The device must maneuver along extremely long corridors, around life support systems and around monitoring systems or traction devices. The device must also move in and out of elevators, through doorways, up wheelchair ramps, over carpeting and tile, and across small open thresholds.

A problem is presented by the mobilization of scintillation camera equipment which is used to detect gamma ray photons emitted from a body in which a radioisotope has been infused to produce a diagnostic image of the patient. Scintillations occur where photons are absorbed by crystalline material. The scintillations are received by a detector head which contains scintillation crystals, photomultiplier tubes and lead shielding. A typical system is based on the camera of Anger, as disclosed in U.S. Pat. No. 3,011,057, and is herein incorporated by reference. The detector head, along with the suspension arm, weighs approximately 300 pounds. The suspension system and column for the detector head add more weight along with the very high density of electronic instrumentation used to analyze and display the diagnostic images of the patient. The substantial size and weight of the diagnostic equipment requires a similarly substantial chassis and mobility drive system to transport the equipment. The combined equipment and mobility chassis weighs over 2,000 pounds and presents the problem of safely maneuvering, steering and braking the device while it is being moved and then stabilizing the device once it is in position.

A particular problem associated with the mobile diagnostic device is that of providing limited visibility to the operator. The device is normally controlled with steering handles located at the rear by an operator walking behind the device. The substantial size of the equipment permits the operator to view only along the left or right side of the device. The visibility of the operator is significantly limited to the front and opposite side of the device. The 2000 pound mass traveling at 3 feet per second could present a hazard to any unseen person or obstacle in the path of the device. In addition to detecting an obstacle in the path of the device, it is important to instantly respond and apply the brakes to avoid colliding with close proximity obstacles. This problem is particularly acute while passing through intersections and while turning corners within the hospital.

Accordingly, one object of the present invention is to provide a diagnostic device which can be safely operated at relatively high speeds through corridors of a hospital.

Another object is to provide a diagnostic device which can be safely controlled by an operator walking behind the device.

Still a further object of the present invention is to provide a diagnostic device which automatically stops when an obstacle is in the immediate path of the device.

SUMMARY OF THE INVENTION

The invention is directed to a proximity detector system for a mobile medical diagnostic device, such as scintillation camera equipment, which can be quickly and safely maneuvered within a hospital. In the scintillation camera example, the chassis for the device includes two forward support wheels having electrically actuated brakes and a single central steerable wheel assembly at the rear of the device. The central rear wheel is also the drive wheel having a bidirectional variable speed electric motor adapted as a self-propelling means. The device is controlled by twin synchronized handles located approximately waist high at the rear of the device and which readily respond to wrist action of an operator walking behind the device.

The method for detecting an obstacle to the front of the device includes the steps of: transmitting ultrasonic sound waves to the front of the device; receiving any waves which are reflected back to the device; analyzing the reflected waves and determining if any obstacle is to the immediate front of the device. Sound waves reflected from the front structure of the device are eliminated from consideration by the introduction of a delay function in the window-establishing function of the analysis step. If it is determined that an obstacle is to the immediate front of the device (within the window), then the brakes are automatically actuated.

The proximity detector system includes an array of transmitting transducers arranged along the front of the device. An ultrasonic transmitter provides electrical signals to the transducers. The transducer converts the signals to sound waves and projects the sound waves to the front of the device. Any array of receiving transducers are arranged adjacent to the transmitting transducers for receiving any sound waves reflected back to the device. The receiving transducers convert the reflected sound waves to electrical signals. The system includes circuitry for analyzing the reflected signals to determine if an obstacle is to the immediate front of the device and for initiating the electrical brakes whenever it is determined that an obstacle is to the immediate front of the device.

BRIEF DESCRIPTION OF THE DRAWINGS

While the novel features of the invention are set forth with particularity in the appended claims, the invention will be understood along with other features thereof from the following detailed description taken in conjunction with the drawings in which:

DETAILED DESCRIPTION OF THE DRAWINGS

Figure 1:
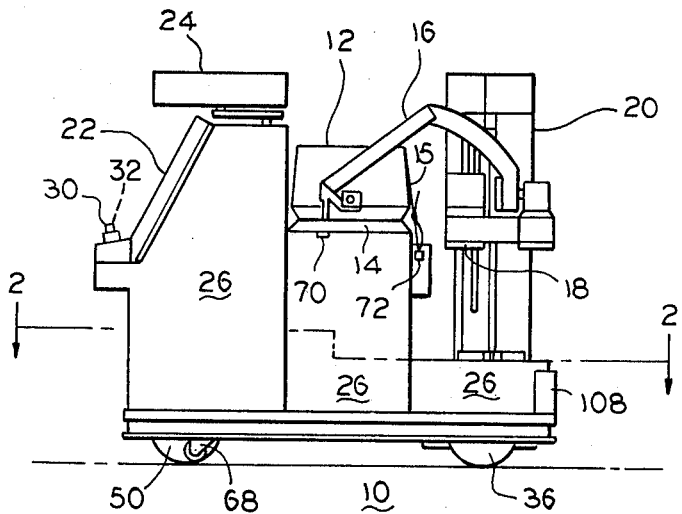
FIG. 1 is a side elevation view of a mobile scintillation camera device incorporating the invention.

Referring first to FIG. 1, there is shown a mobile scintillation camera device 10 in position for being moved within a hospital. The detector head 12 contains the scintillation crystals, photomultiplier tubes and lead shielding for receiving gamma ray energy. During analysis, the detector head 12 is positioned over the patient; however, the detector head is shown in the transportable position resting on a support pad 14 and secured by a hold down strap 15. The detector head 12 is supported by a suspended arm 16 cantilevered from a suspension system indicated by numeral 18. The suspension system 18 is contained within a vertical column structure 20 and controls the vertical position of the detector head 12 at desired positions along the vertical column structure. A control console 22 contains camera electronics, imaging oscilloscopes, and controls for accessory equipment for data analysis. The diagnostic image from the patient is normally displayed at persistance oscilloscope 24. Enclosed within housings 26 (but not shown) are a counterpoise and rotation system for column 20, the storage batteries for providing d.c. power, and all of the electronics and circuitry for the equipment and mobility for the device. The device 10 utilizes conventional 115 volt a.c. power for detection, imaging and data processing during analysis of the patient and utilizes the storage batteries for d.c. power for the mobility systems used to maneuver the device to desired locations within the hospital. The mobility controls are located approximately waist high at the rear of the device. The controls include a right handle assembly 30 and a left handle assembly 32 which are synchronized so that the device can be controlled by either or both hands of the operator.

Figure 2:
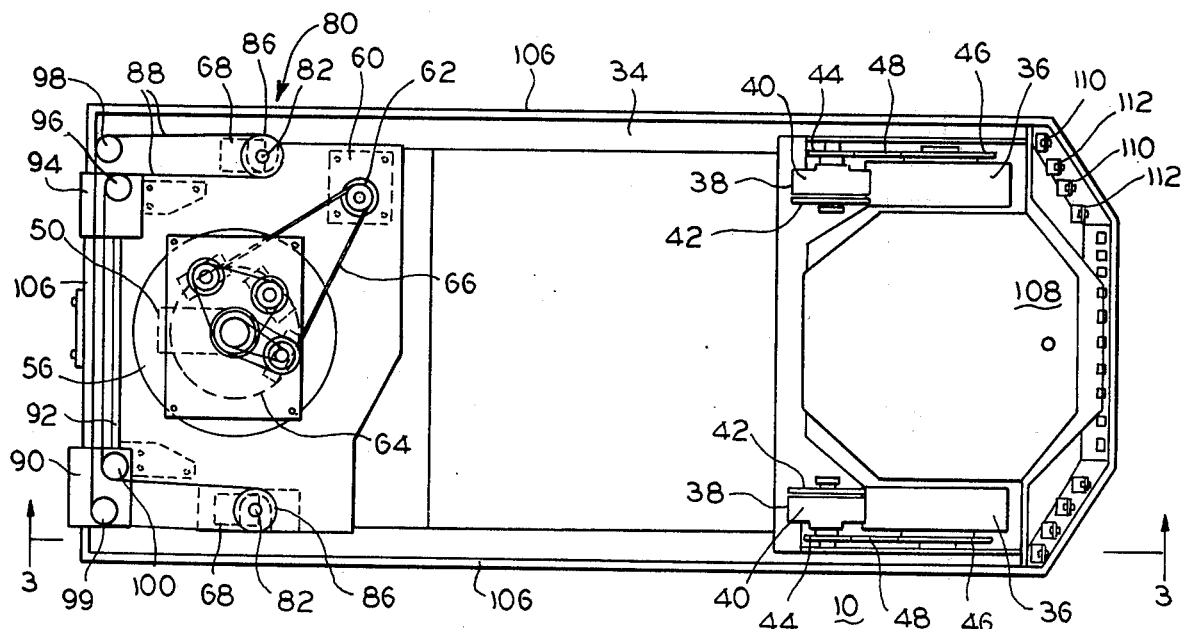
FIG. 2 is a sectional view of the chassis of the device taken along line 2—2 of FIG. 1.
Figure 3:
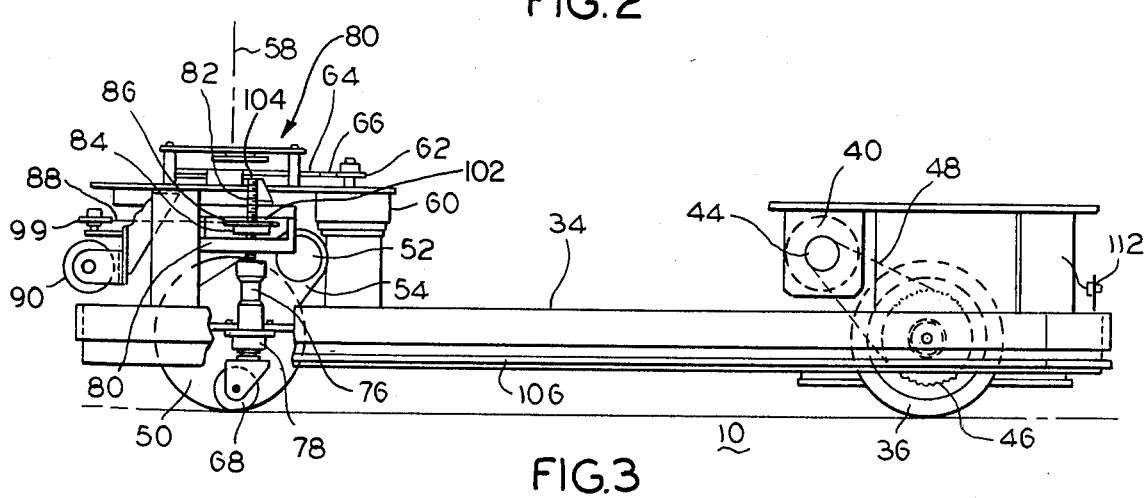
FIG. 3 is a sectional view of the chassis system taken along line 3—3 of FIG. 2.

Referring now to FIGS. 2 and 3, there are shown the features of the chassis mobility systems. The mobility systems are supported by and attached to a rectangular frame 34 surrounding the device 10. The front of the device is supported by two wheel assemblies 36 attached by conventional bearing housings to frame 34. The primary braking system for the device is provided by proportional electromechanical brakes 38. The brakes 38 utilize an electromagnetic coil within a housing 40 and an engagable magnetic disc 42 having an abrasive surface. The amount of engagement by the disc 42 and housing 40 is proportional to the amount of current applied to the electromagnetic coil. The brakes 38 are connected by brake sprockets 44 to wheel sprockets 46 by a continuous chain 48.

The rear of the device 10 is supported by a central, steerable wheel assembly 50. The three-wheeled mobility system permits the device to be extremely maneuverable. In this example, the central wheel assembly 50 is also the drive wheel having means for self-propelling the device 10. The self-propelling means is provided by a bidirectional variable speed motor 52 coupled to the wheel assembly 50 by a conventional gear drive 54. The wheel assembly and self-propelling means are mounted to a rotatable bearing platform 56 having a vertical axis of rotation 58 and mounted to frame 34. The steerable wheel assembly 50 is coupled to a bidirectional steering motor 60 by a steering drive sprocket 62 and a steering wheel sprocket 64 connected by a continuous chain 66.

Several features of the device are described having sprocket and chain drive systems. It should be understood that various gear trains or belt drive systems could be employed in alternative embodiments.

The system includes circuitry such that the handle assemblies 30 and 32 control the steering motor 60 which controls the left or right direction of device 10; and control the motor 52 which controls the forward or rearward direction and velocity of the device.

The three-wheeled mobility system provides a very compact and maneuverable system for controlling and transporting the device. However, when the scintillation camera is positioned for analysis and the heavy detector head 12 is extended to the side of the device over the patient, the three-wheeled mobility system does not provide a stable support for the device. In order to provide a more stable support for the device during diagnostic analysis, a stabilization system is provided having extendable casters 68 near the rear corners of the device. The stabilization system is automatically actuated when an a.c. power cord of the device 10 is plugged into a wall outlet and the detector head 12 is lifted from the support pad 14. A magnetic tape switch 70 is provided under support pad 14 and a sensing microswitch 72 is provided at the end of the detector head hold down strap 15 (as shown in FIG. 1) which must both be closed to indicate that the detector head is lifted from the support pad in order to actuate the system. The casters 68 have vertical shafts 76 which are slideable through bearing journals 78 attached to frame 34. Each caster drive assembly 80 includes a lead screw 82 driven by a confined rotatable nut 84, which is rotated clockwise or counterclockwise by a sprocket 86 and a continuous chain 88. The stabilization system is operated by a bidirectional, split-phase stabilization motor 90 having an output shaft 92 coupled to a gear box 94. The gear box 94 has a drive gear sprocket 96 coupled to the continuous chain 88. Idler sprockets 98, 99 and 100 are provided to synchronize the two caster drive assemblies to the drive gear sprocket 96. During operation, when the device is plugged into a wall outlet and the detector head is lifted from the support pad, circuitry is provided such that stabilization motor 90 will automatically operate to drive gear sprocket 96 and rotate the continuous chain 88 thereby rotating the confined nuts 84 which drive the lead screws downward and extend casters 68 until a lower limit switch 102 is actuated. At this time the central steerable wheel assembly is raised from the floor and the device is supported by the two front wheels 36 and the two rear stabilizing casters 68. Similarly, when the detector head is placed on the support pad and the hold down strap 15 is secured, the circuitry will again activate the motor 90 in the opposite direction whereby the casters will be retracted until an upper limit switch 104 has been actuated and the stabilization system will again come to rest.

Safety is of the uppermost importance when the device is being moved. If the operator should suddenly release the handle assemblies, 30 and 32, the controls will immediately return to a neutral position and the brake system 38 will automatically be applied. A touch sensitive tape 106 extends along the rear and sides of the device. if the tape comes in contact with an obstacle, it deactivates the drive motor 52 and automatically applies the brakes.

In accordance with the present invention, a unique safety feature of the device is a proximity sensor system 108 which detects any obstacles within eighteen inches to the front of the device and automatically applies the brakes which stop the device before reaching the obstacle. The proximity sensor system 108 is an ultrasonic transmitter/receiver which incorporates 27 acoustic transducers arranged above the front bumper of the device. Thirteen of the transducers are dedicated to transmitting and are identified by numeral 110, and fourteen of the transducers are dedicated to receiving the reflected signal and are identified by numeral 112. If there are no obstacles within 18 inches of the front bumper, there will be no reflected signal applied, but as an obstacle moves into 18 inch field, the amplitude of the reflected signal is applied and a "brake command" signal is produced, which actuates the brakes to stop the device within 18 inches of travel.

Figure 4:
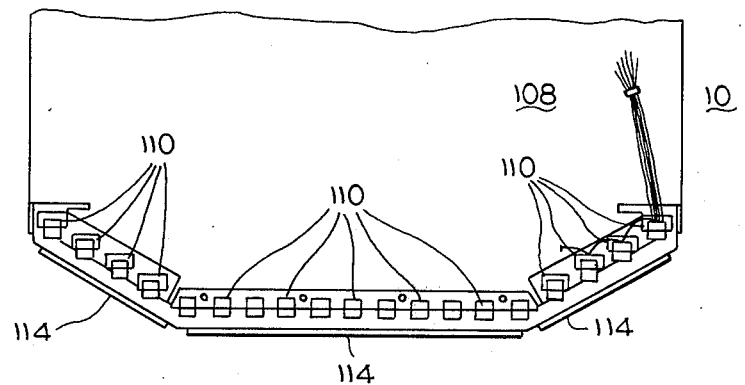
FIG. 4 is an enlarged view of the proximity detector system shown in FIG. 2.
Figure 5:
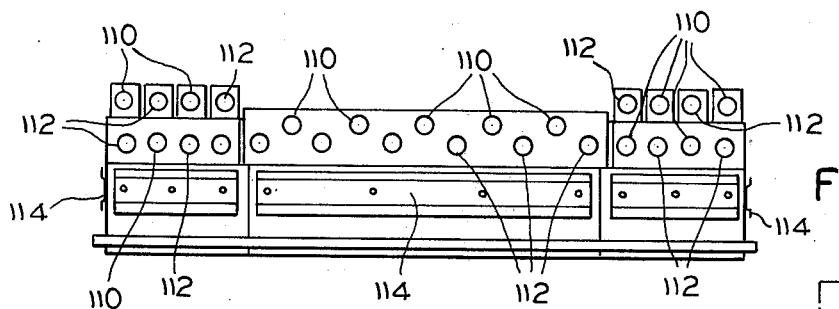
FIG. 5 is a front elevation view of the system shown in FIG. 4.

Referring particularly to FIGS. 4 and 5, the proximity detector 108 system is described in more detail. The thirteen transmitting transducers 110 are shown arranged generally evenly above the front bumper 114 of the device. The fourteen receiving transducers 112 are similarly arranged generally evenly above the front bumper in an alternating adjacent pattern to the transmitting transducers. This pattern provides an even distribution of the ultrasonic waves directed in advance of the device and provides that any reflected waves will be received by the receiving transducers. In alternative embodiments, all of the transducers could be used for both transmitting and receiving with the appropriate circuitry. A suitable ultrasonic transducer is available from MASSA Corp. under part no. MK 109C. The basic method for detecting an obstacle in front of the device comprises transmitting ultrasonic sound waves in advance of the device, receiving any waves which are reflected back to the device, analyzing the reflected waves and determining if any obstacle is to the immediate front of the device, and finally initiating the electrically actuated brakes whenever it is determined that an obstacle is to the immediate front of the device.

Figure 6:
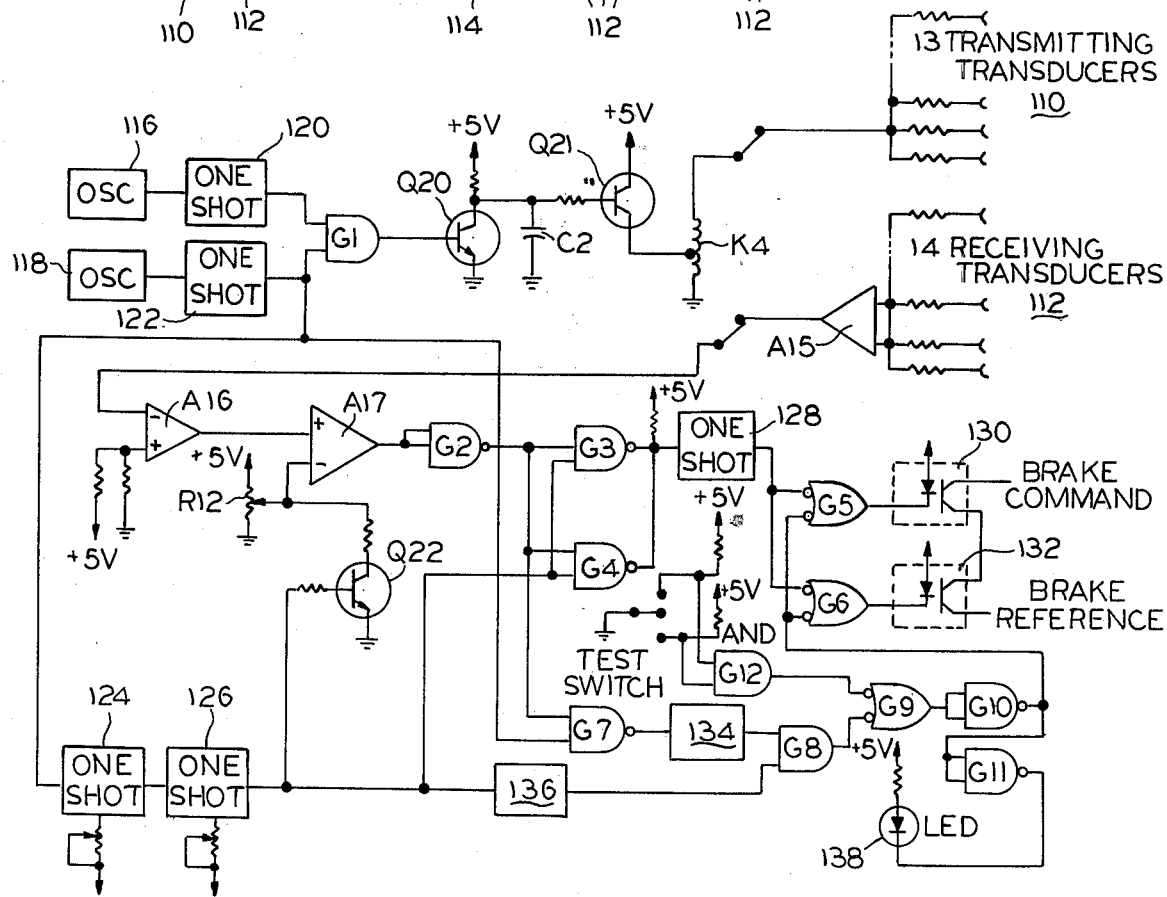
FIG. 6 is a schematic diagram of the circuitry for the proximity detector system.
Figure 7:
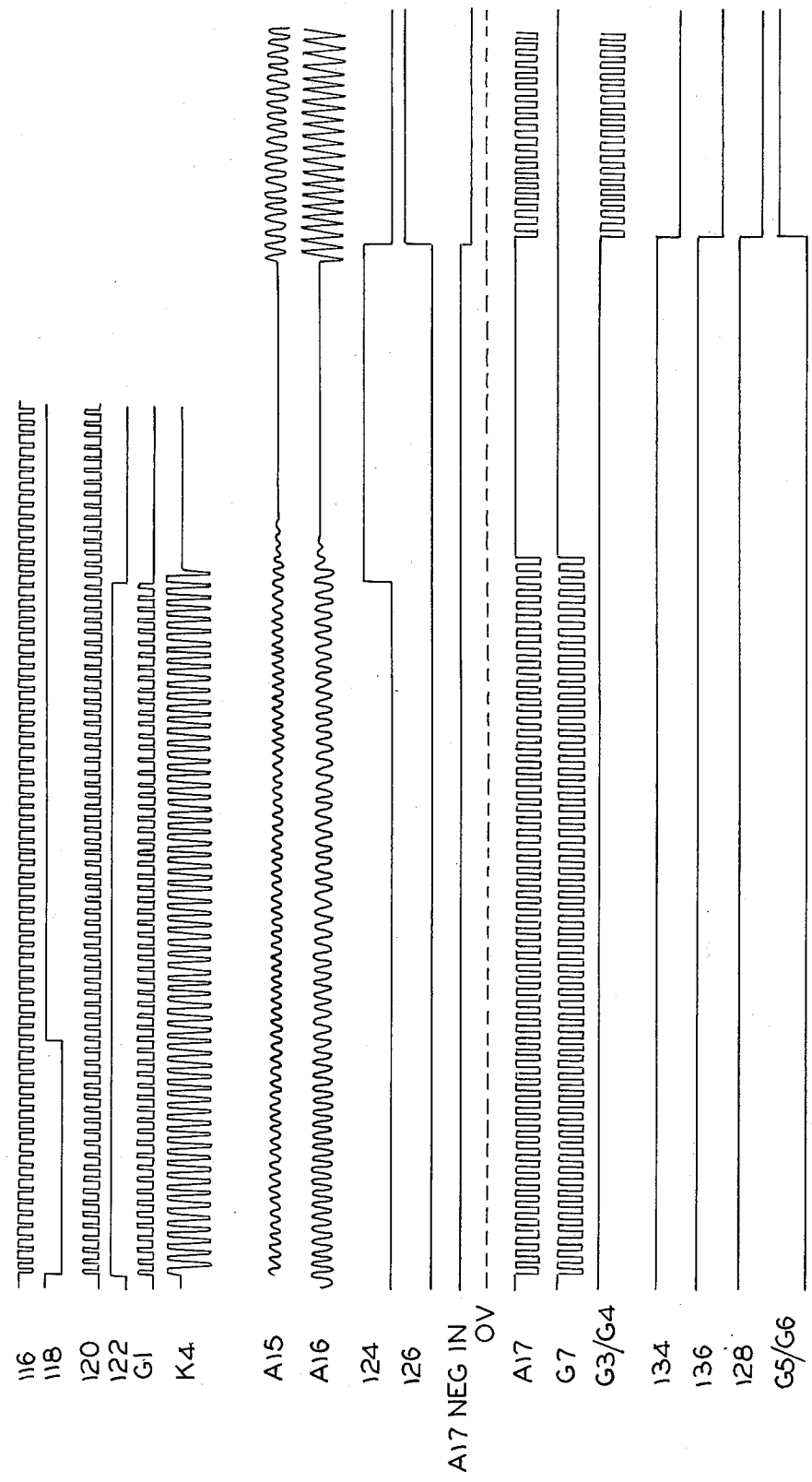
FIG. 7 shows the wave forms incidental to operation of the system shown in FIG. 6.

Referring now to FIGS. 6 and 7, FIG. 6 shows the schematic diagram of the proximity detector circuit and FIG. 7 shows the timing and wave outputs of the respective elements of FIG. 6. Two oscillators 116 and 118 are used to generate the transmitted signal and transmit/receive timing. The first oscillator 116 provides a 40 Khz signal that is applied to a monostable multivibrator, referred to as a one shot 120 which provides an output pulse of approximately 6 μsec at a 40 Khz frequency. The second oscillator 118 controls the transmitter repetition rate. It is set for a maximum oscillation time (in this case, about 80 msec) and is applied to another one shot 122 which provides an output pulse of approximately 1.5 msec at a frequency of 12.3 Hz. The output of each one shot 118 and 122 is applied to a NAND gate G1. The resultant output signal from G1 is a 40 Khz modulated burst at a 12.3 Hz repetition rate. This signal is inverted and applied to a transistor Q20 through a capacitor C2 which shapes the pulses and to another transistor Q21 and through an auto-transformer K4 which provide the proper voltage level to the signals to drive the transmitting transducers 110.

The receiving circuit can be described in the following general functions. The signals received by the receiving transducers are applied to a preamplifier where they are summed and amplified. The signals are then further amplified and offset to a d.c. level, then applied to a comparator. The comparator receives interaction signals and any reflected signals from the receiving transducers and it further receives range window signals which correspond to the intervals at which a sound wave would be reflected from an obstacle a preselected distance in front of the device. The signals from the comparator pass through logic which produce a brake signal, when the amplitude of the reflected signal indicates an obstacle.

The transmitter repetition pulse from one shot 122 is used for the input to two one shots 124 and 126 that form the range window signal. The first one shot 124 outputs a 700 μsec pulse that drives the second one shot 126, causing a delay from the transmitted signal. The output from one shot 126 is a pulse adjustable from 360 μsec to 3.8 msec wide called the range window signal. The larger the pulse width, the further the distance from the front of the unit that the brake signal will be generated when an obstacle is detected by the system. In this embodiment, the range window is set at 1.5 msec for obstacles at a distance of 18 inches to the front of the device. The signals received by the fourteen receiving transducers 112 are applied to a preamplifier A15 which sums the output of the transducers and preamplifiers the signal by a gain of 10 to 100, depending upon the number of transducers that pick up the signal. The preamplified signal is about ½ volt peak-to-peak due to a received interaction signal from the transmitting transducers, and is about one volt peak-to-peak when an echo signal is received. The preamplified signal is applied to the input of an inverting operational amplifier A16. A16 amplifies the signal by a gain of 5 and offsets the signal by 2.5 volts with R10 and R11. The output from A16 is applied to the plus input of a comparator A17. The negative input to the comparator A17 is normally about 2.2 volts selected at R12. To compensate for the gain differences between the transmitter-receiver interaction signals and the echo signals, the negative comparator input voltage level is decreased during the receive time. When a range window signal is generated, the window pulse turns on a transistor Q22 that draws the negative input of A17 down to about 1.6 volts. The output of comparator A17 consists of a high signal which pulses whenever a signal is detected, either during the transmitting portion of the cycles or when an echo is received. This signal is inverted at G2 and applied to a NAND gate G3 with the range window signal. Another NAND gate G4 is connected in parallel as a component failure safeguard. The output of NAND gate G3 is high unless both the reflected signal is received and the range window signal is detected. The NAND gate G3 drives a falling-edge-triggered retriggerable one shot 128. The inverted output of one shot 128 is applied to a NOR gate G5. The output of NOR gate G5, when high, turns off an opto-isolator 130 and presents a "brake" command to the system. Another NOR gate G6 is connected in parallel with G5 and drives another opto-isolator 132 which is in series with opto-isolator 130. The retriggerable one shot, 128, maintains the "brake" command for approximately one second after the obstacle has been removed. To disable the "brake" command, both opto-isolators must be turned on. If either of the isolators are open or turned off, a brake command will be present. This circuit redundancy improves reliability and safety.

The system includes self-checking circuitry which continuously examines the transducers and circuitry. The self-check feature of the proximity detector operates on the interaction signal which is generated by the reflected signal from the front of the device and by the transmitted signal being conducted through the frame to the receiving transducers. The output of the one shot, 122, and the output of G2 are applied to the NAND gate G7. The output of G7 is high unless both the interaction signal and the 1.5 msec pulse from one shot 122 are present. The output of G7 drives a falling-edge-triggered retriggerable one shot, 134, which has a pulse width of 250 msec. The inverted output of one shot 126 is differentiated and applied to the retriggerable one shot, 136, which also has a pulse width of 250 msec. The output of each one shot 134 and 136 is applied to a positive AND gate G8. The output of G8 is high for normal operation of the detector system, which requires that both one shots, 134 and 136, be triggered. The one shot 134 checks the entire transmitter, amplifiers A15 and A16, comparator A17 and gate G2. The one shot 134 will remain triggered as long as all of components it is checking are functioning properly. The one shot 136 will be triggered as long as one shot 124 and 126 are functioning properly. The output of G8 drives the input of a NOR gate G9. The output of G9, which is normally low, is inverted at a NAND gate G10. The output of G10 drives an input of the NOR gates G5 and G6 and the input of a NAND gate G11, which drives a light emitting diode 138 which indicates the status of the self-checking circuitry. The LED 138 will be off if the check fails or if an obstacle is detected. The outputs of gates G5 and G6 drive the opto-isolators 130 and 132. A low at either input of gate G8 will cause a high at the outputs of gates G5 and G6, turning off the opto-isolators 130 and 132 presenting a "brake" command to the system. A secondary "brake" command channel, if one shot 128 should fail, is provided by the following sequence. The output of gate G3 also drives the reset inputs of one shots 134 and 136, causing a low at the output of gate G8 which turns off the opto-isolators 130 and 132 presenting a "brake" command to the system. The self-check feature of the system has been incorporated to add to system safety by checking the signal flow of the proximity detector system.

While a specific embodiment of the present invention has been illustrated and described herein, it is realized that modifications and changes will occur to those skilled in the art. It is, therefore, to be understood that the appended claims are intended to cover all such modifications and changes as fall within the true spirit and scope of the invention.

What is claimed is:

1. A method for detecting an obstacle to the immediate front of a mobile medical diagnostic device having a front portion comprising the steps of:
   generating transmission signals,
   in response to said transmission signals, transmitting ultrasonic sound waves from transducers located behind the device front portion to and in advance of the front portion of the device and generating range window signals which correspond both to time intervals at which said sound waves would be reflected from an obstacle at a preselected distance in front of the device and to a predetermined time period corresponding to the distance from the transducers to the device front portion,
   receiving any waves that are reflected back to the transducers and converting said reflected waves to reflected signals, and
   processing said reflected signals and said range window signals to determine whether an obstacle is within said preselected distance from the front of the device.

2. An obstacle detector system for a mobile medical diagnostic device having a front portion, comprising:
   means for generating transmission signals,
   means responsive to said transmission signals for transmitting ultrasonic waves from transducers located behind the device front portion to and in advance of the front portion of the device,
   means for generating range window signals in response to said transmission signals, said range window signals corresponding both to time intervals at which said sound waves would be reflected from an obstacle at a predetermined distance in front of the device and to a predetermined time interval at which said sound waves would be reflected back to the transducers from the front portion of the device,
   means for receiving any waves which are reflected back to the device, and
   circuitry means for analyzing the reflected waves and, with the use of the range window signals, determining if an obstacle is to the immediate front of the device.

3. The obstacle detector system as recited in claim 2 wherein said transmitting means comprises:
   an array of transmitting transducers arranged along the front bumper of the device,
   an ultrasonic transmitter which provides an electrical signal to said transmitting transducers,
   said transmitting transducers for converting the electrical signal to sound waves and projecting the sound waves to the front of the device.

4. The obstacle detector system as recited in claim 2 wherein said receiving means comprises:
   an array of receiving transducers arranged along the front of the device,
   said receiving transducers for receiving any sound waves reflected back to the device and converting the sound waves to electrical signals.

5. The obstacle detector system as recited in claim 3 wherein said array of transmitting transducers includes approximately 13 said transmitting transducers arranged generally evenly along the front of the device.

6. The obstacle detector system as recited in claim 4 wherein said array of receiving transducers includes approximately 14 said receiving transducers arranged generally evenly along the front of the device.

7. The obstacle detector system as recited in claim 3 wherein said ultrasonic transmitter comprises:
   a first oscillator which provides an oscillating signal,
   a second oscillator which provides a repetition rate signal,
   a transmit gate which receives the first oscillator signal and the repetition rate signal and provides a time modulation pulsed signal, a pulse shaper which shapes the time modulation pulsed signal received from said transmit gate, and a transmit driver which provides the proper voltage level to the signals to drive said transmitting transducers.

8. The obstacle detector system as recited in claim 2 wherein said range window signal generator means provides a range window signal which corresponds to a sound wave which would be reflected from an obstacle approximately 8 inches to the front of the device.

9. The obstacle detector system as recited in claim 2 which further comprises circuitry means for self-testing the system.

10. The obstacle detector system as recited in claim 9 wherein said self-testing circuitry means continuously analyzes said transmitting means, said receiving means and said reflected wave analyzing means and initiates the brake system if any said means malfunctions.

11. A method as set forth in claim 1 wherein the device includes an electrically actuated brake and including the step of initiating the electrically actuated brake when it is determined that an obstacle is within said preselected distance from the front of the device.

12. An obstacle detector system as set forth in claim 2 wherein said device includes an electrically activated brake system and means for initiating the brake system when it is determined that an obstacle is to the immediate front of the device.

* * * * *